(12) United States Patent
Mahoor et al.

(10) Patent No.: US 10,588,534 B2
(45) Date of Patent: Mar. 17, 2020

(54) MOTOR TASK DETECTION USING ELECTROPHYSIOLOGICAL SIGNALS

(71) Applicant: Colorado Seminary, which owns and operates the University of Denver, Denver, CO (US)

(72) Inventors: Mohammad H. Mahoor, Lone Tree, CO (US); Soroush Niketeghad, Los Angeles, CA (US); Adam O. Hebb, Englewood, CO (US); Sara J. Hanrahan, Denver, CO (US); Joshua Nedrud, Aurora, CO (US); Hosein M. Golshan, Denver, CO (US)

(73) Assignee: Colorado Seminary, which owns and operates the University of Denver, Denver, CO (US)

( * ) Notice: Subject to any disclaimer, the term of this patent is extended or adjusted under 35 U.S.C. 154(b) by 415 days.

(21) Appl. No.: 15/369,707

(22) Filed: Dec. 5, 2016

(65) Prior Publication Data
US 2017/0156622 A1 Jun. 8, 2017

Related U.S. Application Data

(60) Provisional application No. 62/263,173, filed on Dec. 4, 2015.

(51) Int. Cl.
*A61B 5/04* (2006.01)
*A61B 5/0484* (2006.01)
(Continued)

(52) U.S. Cl.
CPC ........ *A61B 5/0484* (2013.01); *A61B 5/04012* (2013.01); *A61N 1/0534* (2013.01);
(Continued)

(58) Field of Classification Search
None
See application file for complete search history.

(56) References Cited

U.S. PATENT DOCUMENTS

| 2006/0173510 A1* | 8/2006 | Besio | A61B 5/0482 |
| | | | 607/45 |
| 2009/0062696 A1* | 3/2009 | Nathan | A61B 5/1107 |
| | | | 600/595 |

(Continued)

OTHER PUBLICATIONS

Lepage et al. A statistically robust EEG re-refering procedure to mitigate reference effect. Journal of Neuroscience Methods, Sep. 30, 2014; 235; 101-116. (Year: 2014).*

*Primary Examiner* — Etsub D Berhanu
(74) *Attorney, Agent, or Firm* — Maschoff Brennan

(57) ABSTRACT

Systems and methods are disclosed to detect and/or classify electrophysiological signals as motor events. In some embodiments, a method may include: recording a first plurality of electrophysiological signals from a first plurality of probes inserted into the left hemisphere of the brain; recording a second plurality of electrophysiological signals from a second plurality of probes inserted into the right hemisphere of the brain; pre-processing the first plurality of electrophysiological signals and the second plurality of electrophysiological signals; bipolar re-referencing the first plurality of electrophysiological signals and the second plurality of electrophysiological signals; determining an optimal pair of electrophysiological signals from the bipolar re-referenced first plurality of electrophysiological signals and the bipolar re-referenced second plurality of electrophysiological signals; matching the optimal pair of electrophysiological signals with a template; and detecting motor events from the matching.

18 Claims, 10 Drawing Sheets

(51) Int. Cl.
*A61N 1/05* (2006.01)
*A61N 1/36* (2006.01)
*A61B 5/00* (2006.01)
*A61B 5/0478* (2006.01)
*A61B 5/11* (2006.01)

(52) U.S. Cl.
CPC ........ *A61N 1/36067* (2013.01); *A61B 5/0478* (2013.01); *A61B 5/11* (2013.01); *A61B 5/4082* (2013.01)

(56) References Cited

U.S. PATENT DOCUMENTS

| | | | | |
|---|---|---|---|---|
| 2009/0099627 | A1* | 4/2009 | Molnar | A61B 5/04014 |
| | | | | 607/62 |
| 2009/0221928 | A1* | 9/2009 | Einav | A61B 5/0484 |
| | | | | 600/544 |
| 2014/0031711 | A1* | 1/2014 | Low | A61B 5/16 |
| | | | | 600/544 |
| 2017/0301214 | A1* | 10/2017 | Chen | A61B 5/6843 |

* cited by examiner

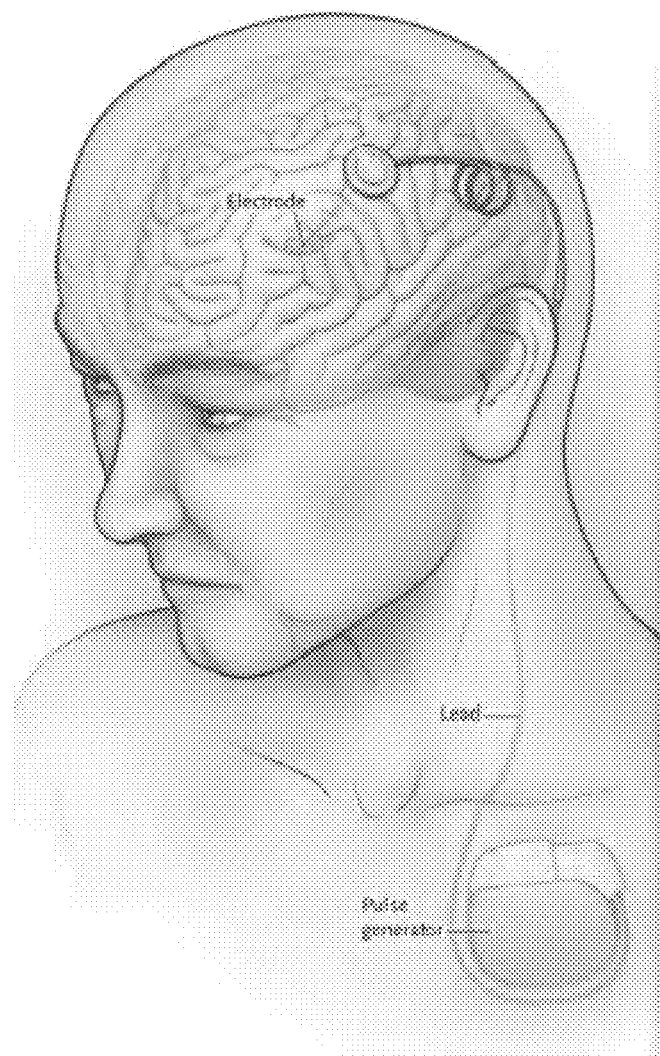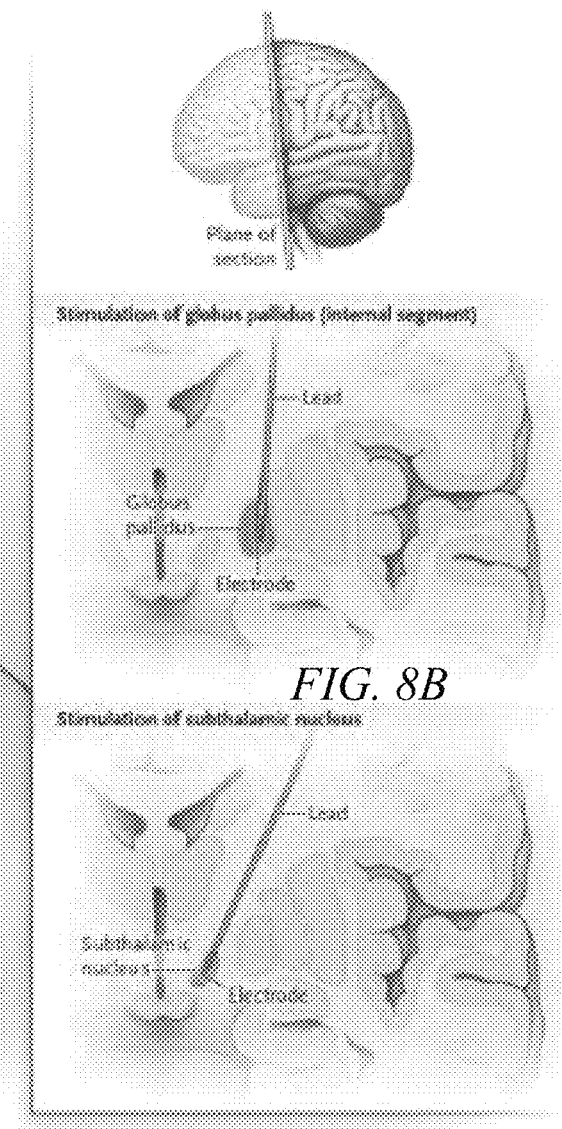
FIG. 8A
FIG. 8B
FIG. 8C

MOTOR TASK DETECTION USING ELECTROPHYSIOLOGICAL SIGNALS

CROSS-REFERENCE TO RELATED APPLICATIONS

This application is a non-provisional claiming priority benefit of U.S. provisional patent Ser. No. 62/263,173, filed on Dec. 4, 2015, titled "MOTOR TASK DETECTION USING BRAIN SUBTHALAMIC NUCLEUS LOCAL FIELD POTENTIALS."

BACKGROUND

Parkinson's disease is a chronic and progressive neurodegenerative disorder pertaining to the central nervous system. Although, the main cause of this phenomenon is still unknown, some studies show the interaction of distinct processing circuits of the basal ganglia and cortex may be involved. The symptoms of PD appear by the malfunction and death of dopamine-generating cells in an area of the brain called substantia nigra. The lack of these vital neurons causes various motor disorders including tremor, rigidity, bradykinesia, and postural instability Although, there is currently no certain cure for PD, there are different kinds of treatment options such as medication and surgery to alleviate the disorder manifestations. In recent years, Deep Brain Stimulation (DBS) has been considered as an effective treatment to deal with PD, specifically when drug therapy is no longer sufficient. Using high frequency (~130-185 Hz) electrical pulses, DBS stimulates specific targets in the brain including the subthalamic nucleus. This procedure is done through surgically implanted electrodes that are supplied by a battery-powered implanted pulse generator

SUMMARY

Some embodiments discussed in the present disclosure are related to the asynchronous detection of movement.

Systems and methods are disclosed to detect and/or classify electrophysiological signals as motor events. In some embodiments, a method may include: recording a first plurality of electrophysiological signals from a first plurality of probes inserted into the left hemisphere of the brain; recording a second plurality of electrophysiological signals from a second plurality of probes inserted into the right hemisphere of the brain; pre-processing the first plurality of electrophysiological signals and the second plurality of electrophysiological signals; bipolar re-referencing the first plurality of electrophysiological signals and the second plurality of electrophysiological signals; determining an optimal pair of electrophysiological signals from the bipolar re-referenced first plurality of electrophysiological signals and the bipolar re-referenced second plurality of electrophysiological signals; matching the optimal pair of electrophysiological signals with a template; and detecting motor events from the matching.

In some embodiments, the optimal pair of electrophysiological signals are determined by performing a nonlinear regression on the bipolar re-referenced first plurality of electrophysiological signals and the bipolar re-referenced second plurality of electrophysiological signals.

In some embodiments, the nonlinear regression may produce a measure of inter-correlation between each of the bipolar re-referenced first plurality of electrophysiological signals and each of the bipolar re-referenced second plurality of electrophysiological signals.

In some embodiments, the optimal pair of electrophysiological signals are determined from a time-frequency transform applied to the electrophysiological signals.

In some embodiments, the optimal pair of electrophysiological signals with a template includes applying a principal component analysis on the template and the bipolar re-referenced first plurality of electrophysiological signals and the bipolar re-referenced second plurality of electrophysiological signals to obtain normalized correlation coefficients.

In some embodiments, bipolar re-referencing the first plurality of electrophysiological signals and the second plurality of electrophysiological signals further comprises: subtracting each of the first plurality of electrophysiological signals from another of the first plurality of electrophysiological signals; and subtracting each of the second plurality of electrophysiological signals from another of the second plurality of electrophysiological signals.

In some embodiments, the method may include determining an optimal first electrophysiological signal and an optima second electrophysiological signal from the linear regression.

In some embodiments, the electrophysiological signals comprise local field potential (LFP) signals.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

Example embodiments will be described and explained with additional specificity and detail through the use of the accompanying drawings in which:

FIG. 8A is a drawing showing example placements of an electrode inserted within a human brain.

FIG. 8B is a drawing showing an electrode inserted into the globus pallidus of the human brain.

FIG. 8C is a drawing showing an electrode inserted into the subthalmic nucleus of the human brain.

DETAILED DESCRIPTION

Figure 1:
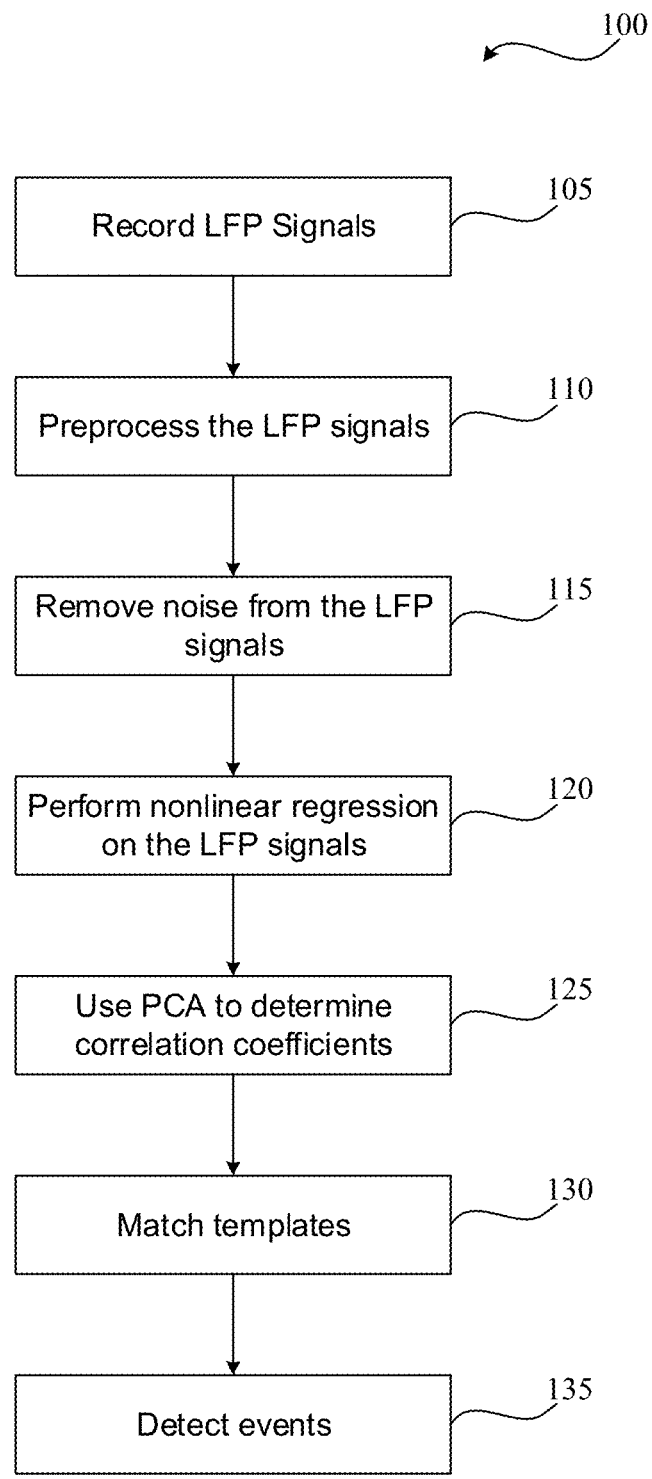
FIG. 1. Illustrates an example flow of operations that may be performed according to some embodiments of the present disclosure.

Some embodiments described in the present disclosure relate to methods and systems of recognizing behavioral activity from neural feedback. The movements may be voluntary by the subject and cued by an instruction.

Deep brain stimulation (DBS) is a treatment method used for movement disorders such as Parkinson's disease, among other things. DBS devices may include electrodes, an extension, and an implantable pulse generator (IPG). The electrodes may be thin, insulated wires inserted through a small opening in the skull and implanted in the brain. The tip of each electrode may be positioned in a specific brain area. A plurality of electrodes may be implanted into each hemisphere of the brain. For example, four, five, six, eight, ten, twelve, fourteen, etc. electrodes may be implanted into each hemisphere. The implantable pulse generator may deliver electrical stimulation to specific areas in the brain that control movement.

The implantable pulse generator may be implanted, for example, under the skin near the collarbone or lower in the abdomen. The IPG may deliver electrical stimulation, for example, to specific areas in the brain that control movement. An example DBS set up including the IPG is shown in FIG. 8A.

As described below, systems and methods are described in the present disclosure in which local field potential may be collected and processed to detect movement by the subject. The LFP signals may be recorded from, for example, 4 electrodes implanted in each hemisphere. The signals may be then bipolar re-referenced by subtracting adjacent contacts. The signals may then be down sampled. Using nonlinear regression the inter-correlation between each bilateral pair of channels may be measured. A linear combination of channels may be selected as a template using principal component analysis (PCA). The correlation between the inter-correlation of each bilateral pair of channels and the template may be calculated to derive the feature vector. Single motor events of movement may be detected by thresholding the values of a feature vector.

In some embodiments, LFP signals may be recorded from both hemispheres of the brain. The LFP signals may be non-stationary, such as, for example, the activity in a given area of the brain spreads to other areas of the brain over time. This may cause a group delay or a phase delay. The group delay, for example, may lead to a constant time delay based on the locations of the leads. The group delay, for example, may or may not distort the signal. Nonlinear methods, such as nonlinear regression, mutual information, or synchronization of phases, for example, may be used to compensate for the group delay due to the distance between the leads.

In some embodiments, preprocessing of the LFP signals may be performed. To preprocess the data, for example, the LFP signals may be bipolar re-referenced by subtracting lead data from adjacent locations in the brain. A phase-filter, for example, may also be applied such as, for example, a zero-phase filter with transient band of 80-100 Hz. The LFP signals may be filtered, for example, after the re-referencing. The data may, for example, be down sampled to 200 Hz.

In these and other embodiments the interdependency between the two hemispheres may be determined based on the pre-processed LFP data such as, for example, via nonlinear regression. For example, in some embodiments, non-parametric nonlinear regression of signals from both hemispheres of the brain may be performed. This method may determine, for example, the dependency between the signals from both hemispheres when the LFP data from one hemisphere is shifted forward in time. Using this method, a nonlinear correlation coefficient may be determined from the highest amount of nonlinear correlation for a limited range of time shifts.

In some embodiments, correlation coefficients corresponding to at least two bilateral pairs may be calculated. A bilateral pair may be, for example, LFP signals from both the left and right hemispheres of the brain, and may, for example, include LFP signals from the same section of the brain on opposing hemispheres. Principal component analysis (PCA) may be applied to each bilateral pair of data to obtain the normalized correlation coefficients. In some embodiments, a template for all of the components may be created and a template matching algorithm may be applied to each component. In some embodiments, receiver operating characteristic (ROC) curves may be calculated and the component corresponding to the highest area under the curve (AUC) is selected as the optimum component.

In some embodiments a template may be created to find occurrences of voluntary movements (such as, for example, pressing a button on cue). There may be a pattern of the LFP signals when movement occurs and the template may reflect this pattern.

Template matching may be performed, for example, after a template has been created. After creating a template the pattern of the preprocessed and nonlinearly regressed data may be analyzed. For example, correlation between the data and a short template may be calculated. A feature vector, for example, may be a time series of normalized correlation coefficients between the template and the most recent segment of real time data. For example, if there is a potentially similar shape between the data and the template, the template may be time-shifted to determine if there is a pattern match. Alternatively or additionally, either the data or the template may be time-shifted in either direction to find a pattern match.

In some embodiments, the feature vector obtained by a template matching method may be fed to a motor event detection block to determine the detected times. In some embodiments, a threshold value of the detection algorithm may be used to classify binary motor events. For example, values above that threshold may be considered detected motor events (e.g., voluntary movement) and values below that threshold may be considered non-motor events (e.g., non-movement).

Modifications, additions, or omissions may be made to the system without departing from the scope of the present disclosure. For example, in some embodiments, the method for detecting asynchronous movement may include any number of other components that may not be explicitly illustrated or described.

FIG. 1 illustrates a flowchart of an example process 100 that may be performed according to some embodiments of the present disclosure. The process 100 is merely an example and variations may be present. As another example, additional blocks or steps may be included. As another example, one or more blocks or steps may not be included. As yet another example, in some embodiments, a prior-created template may be used for template matching and motor event detection. Additionally or alternatively, alternate methods of preprocessing the LFP signals, including performing mutual information or synchronization of phases, may be done to compensate for the group delay. The process 100 may, for example, be executed and/or controlled at least in part with a computational system 1000 shown in FIG. 10.

In some embodiments, at block 105 LFP signals may be recorded using more than one electrode placed in the brain. Any type of system or sensors may be used to detect and/or record LFP signals. For example, a DBS system may detect and record LFP signals.

In some embodiments, at block 110 the LFP signals may be preprocessed. For example, a zero-phase filter with a transient band of 80-100 Hz (or any other frequency band) may be applied to the signals. Alternatively or additionally, the signals may be down sampled to 200 Hz. Various other sampling, amplifying, digitizing, down sampling, filtering, mathematical processing, etc. may be performed on the LFP signals at block 110. In some embodiments, the LFP signals may be amplified, digitized (e.g., 5 kHz), band passed filtered (e.g., 1-100 Hz), and/or combined with motor event markers and/or subject responses.

In some embodiments, at block 115 noise may be removed from the LFP signals. In some embodiments, a bipolar re-referencing may occur that may remove pre-existing average reference projections from the LFP signals. In some embodiments, removing the noise, for example, may remove power line interference (PLI) without any filtering related distortions. In some embodiments, the signals from adjacent electrodes in each hemisphere may be subtracted from each other to remove systematic noise. For example, if three electrodes are being used in a given hemisphere, for a given LFP signal, $LFP_1$, one of the other two LFP signals, $LFP_2$ or $LFP_3$ may be subtracted therefrom. This may be done with each of the three LFP signals.

In some embodiments, signals from each probe may be subtracted from every other probe signal of the same hemisphere or from more than one probe signal from the same hemisphere. For example, if four probes record signals from the left hemisphere, then each probe signal may be subtracted from each of the other three probe signals resulting in nine signals. In some embodiments, if there are N probes, then $(N-1)^2$ signals may be produced by subtracting every probe signal from every other probe signal. Any type of bipolar re-referencing algorithm may be used.

In some embodiments, at block 120, a nonlinear regression of the LFP signals from the left hemisphere and the right hemisphere may be calculated. For example, the non-linear regression may be based on an estimation of nonlinear correlation between the signals from the left hemisphere and the right hemisphere. The nonlinear regression, for example, may be performed on the subtracted signals from block 115.

In some embodiments, the nonlinear regression of two LFP signals from different hemispheres may represent the dependency of one signal on the other signal when one signal is shifted forward in time. The nonlinear regression between signal X and signal Y may, for example, be calculated when signal Y is shifted τ samples suing the following:

$$h_{XY}^2(\tau) = 1 - \frac{VAR(Y[n+\tau]) | X[n]}{VAR(Y[n+\tau])},$$

where $VAR(Y[n+\tau]|X[n])$ is the conditional variance of $Y[n+\tau]$ given $X[n]$. In some embodiments, the highest amount of non-linear correlation for a limited range of time shifts may be calculated which may lead to a non-linear correlation coefficient:

$$h_{XY}^{2*} = \max_\tau h_{XY}^2(\tau)$$

In some embodiments, a rectangular window of, for example, one second may be applied to the down sampled signals where the overlap of two consecutive windows may be 90% of the window length. From this a time series of correlation coefficients may be determined.

In some embodiments, at block 125 a principal component analysis (PCA) or a similar process, algorithm, or technique may be used to determine an optimum component. The optimum component may be calculated, for example, for every possible bilateral pair.

For example, a linear combination of LFP signals with optimal coefficients may be created for use in block 130. The coefficients, for example, may be calculated using training data and/or PCA. As another example, the coefficients can be calculated from the following:

$$c_{XY_k}^{2*}[n] = \sum_{k=1}^{N_{ch}^2} \lambda_k c_{X_k Y_k}^{2*}[n].$$

In some embodiments, at block 130 template matching using the normalized correlation coefficient from the non-linear regression may be used to find occurrences of a movement motor event. For example, a template may be created by applying rectangular time windows to each trial and synchronized to form a pattern for each subject over the time interval.

A template may be created in any number of ways. For example, a template may span a known time period (e.g., 1, 2, 3, 4, 5, or more seconds). A template may be created, for example, by averaging a training motor event of a known motor event. In some embodiments, time windows w[n−k] starting a period of time before the onset of the trial $m_i$ are applied to each trial i in the first task block and the results may be synchronized averaged to form a 3 seconds (30 samples) pattern for each subject. A template may, for example, be calculated from:

$$p_{XY}^{2*} = \sum_{i=1}^{N_{trial}} c_{XY}^{2*}[n] w[n - m_i].$$

In some embodiments, a correlation between optimal LFP signals (e.g., a linear combination of LFP signals and/or synchronized LFP signals from process 600) and a template may be determined from:

$$\gamma_{XY}^{2*} = \frac{\Sigma_k p_{XY}^{2*}[k] c_{XY}^{2*}[k-n]}{\Sigma_k p_{XY}^{2*}[k] \Sigma_k c_{XY}^{2*}[k-n]},$$

where $\gamma_{XY}^{2*}$ is time series of normalized correlation coefficients between the template $p_{XY}^{2*}[n]$ and the most recent segments of the optimal LFG signals $c_{XY}^{2*}$.

In some embodiments, at block 135 motor events may be detected based on the template matching performed in block 130. In some embodiments, motor events may be detect in the motor event that the correlation between a template and the optimal LFP signals when the correlation coefficient, γ, is greater than a given threshold. In some embodiments, a binary thresholding algorithm may be used that returns a one value with a motor event has occurred (e.g., when γ is greater than a given threshold) and a zero when a motor event has not yet occurred (e.g., when γ is less than a given threshold). In some embodiments, motor event detection may return a time when the matched motor event occurred.

Figure 2:
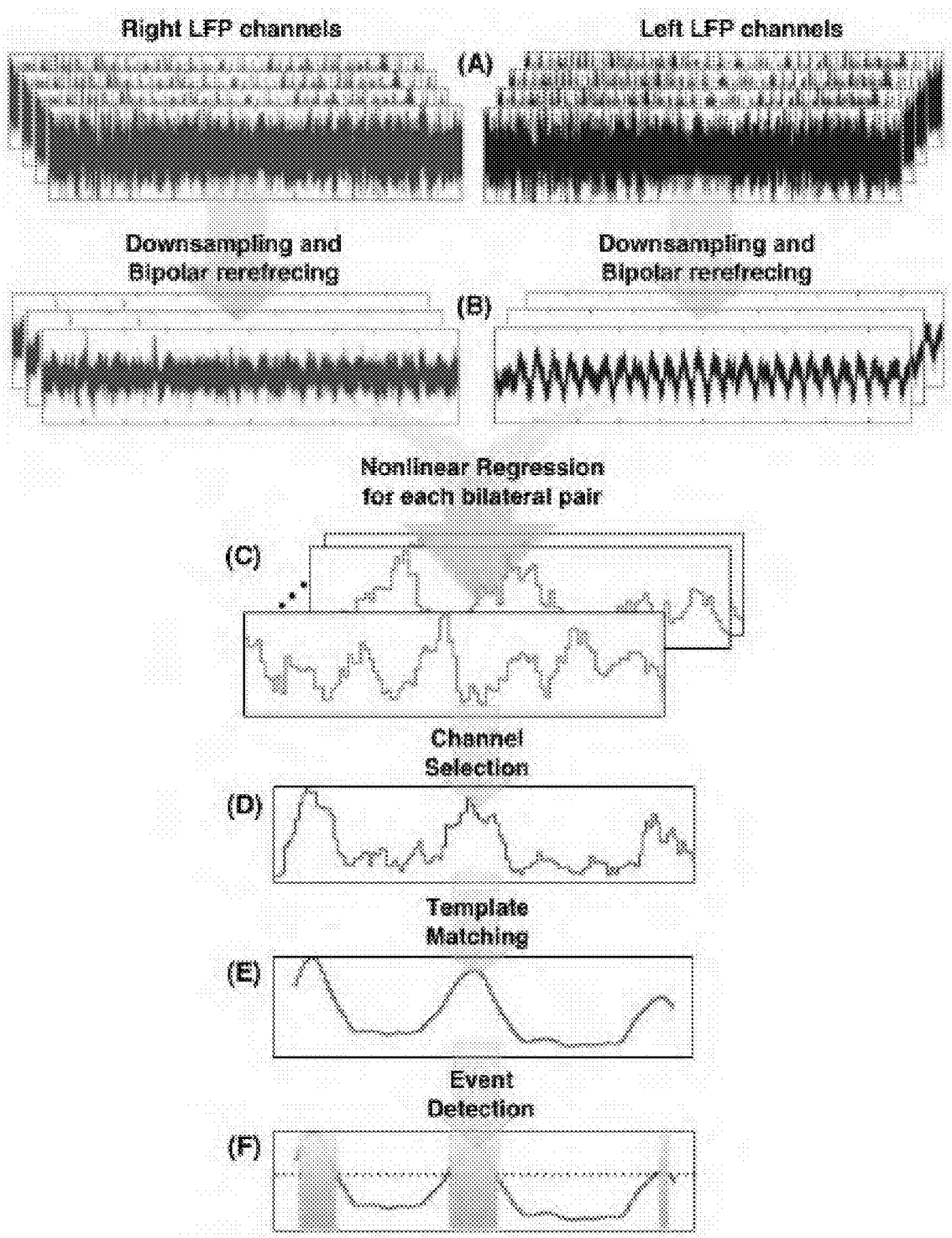
FIG. 2 illustrates an example process according to some embodiments.

FIG. 2 illustrates an example process according to some embodiments. FIG. 2 may, for example, be considered a graphical representation of the process 100 shown in FIG. 1. In this example, at "A" four right LFP signals are recorded and four left LFP signals are recorded for a total of 8 LFP signals. This may be performed, for example, as described above in block 105.

At "B" the LFP signals may be down sampled and/or bipolar re-referenced. This may be performed in a manner similar to what is shown in blocks 110 and/or 115.

At "C" a nonlinear regression may be performed on the signals. The nonlinear regression, for example, may be performed in a manner similar to what is shown in block 120.

At "D" channel selection may occur. Channel selection, for example, may include any process that determines correlation coefficients such as, for example, as shown in block 125, and uses the correlation coefficients to select channels.

At "E" template matching may occur, which may be similar to block 130.

At "F" motor event detection may occur, which may be similar to block 135.

Figure 3:
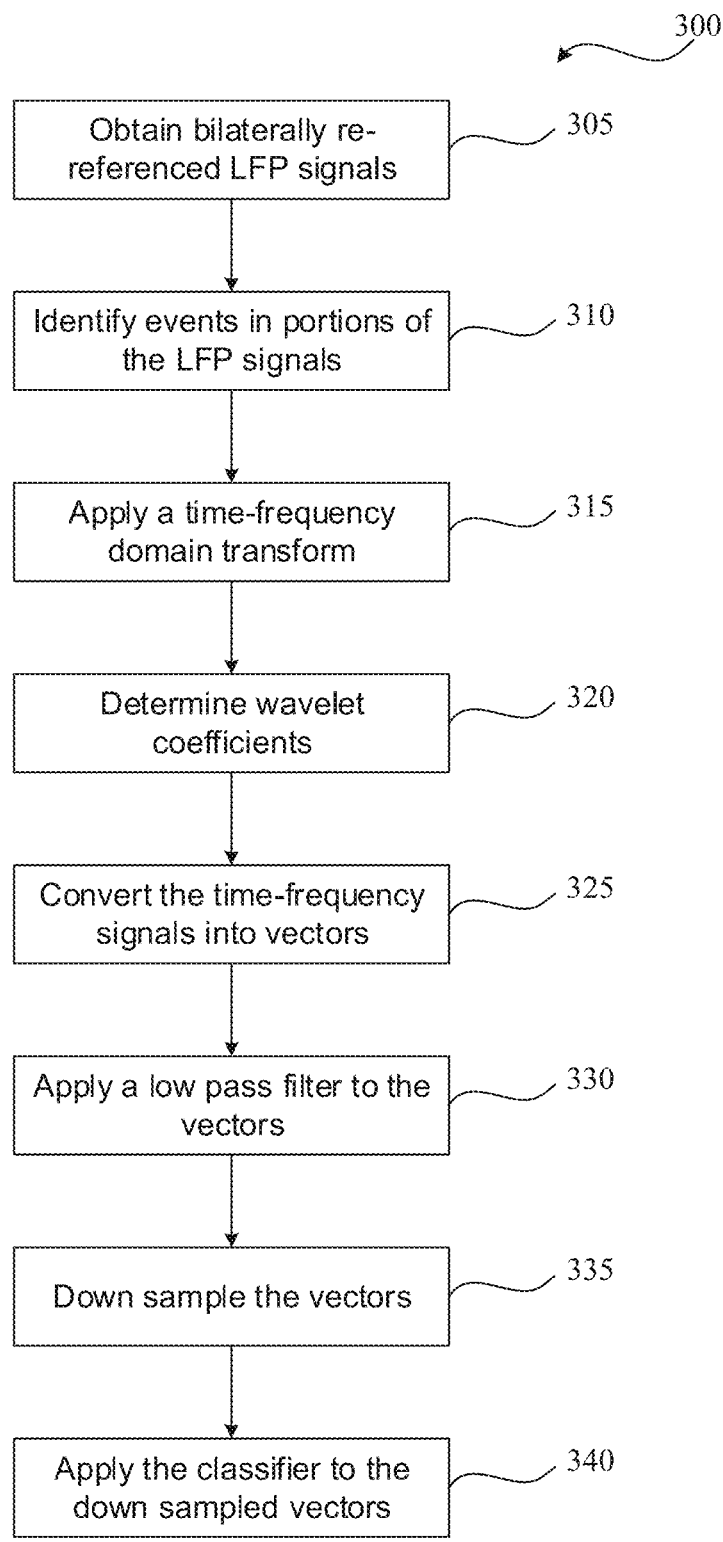
FIG. 3 illustrates a flowchart of an example process 300 that may be performed according to some embodiments

FIG. 3 illustrates a flowchart of an example process 300 that may be performed according to some embodiments of the present disclosure. The process 300 is merely an example and variations may be present. As another example, additional blocks or steps may be included. As another example, one or more blocks or steps may not be included. As yet another example, process 300 may use a time-frequency representation (or spectrogram) of the LFP signal for feature extraction and/or motor event classification. The process 300 may, for example, be executed and/or controlled at least in part with a computational system 1000 shown in FIG. 10.

For instance, different behavioral tasks may yield different representations in the time-frequency domain. Thus, the time-frequency domain may be an appropriate measure to differentiate between various human behaviors.

At block 305, bilaterally re-referenced LFP signals may be obtained. For example, bilaterally re-referenced LFP signals may be obtained via blocks 105, 110, and/or 115. The bilaterally re-referenced LFP signals may be obtained in any possible way.

At block 310, identify motor events in portions of the LFP signals that correspond with a specific motor event. In some embodiments, the motor events in the LFP signals may be identified by correlating the LFP signals with data specifying the time a specific motor event occurred by a patient with electrodes placed within their brain. For instance, a data file may include the time period when a specific motor event occurred along with an identifier specifying the motor event type.

In some embodiments, the portions of the LFP signals may be identified based on the timing. For instance, if a given motor event occurred at a specific time, then the LFP signal data corresponding with the specific time may be identified. In some embodiments, a time window may be identified. The time window, for example, may have a specific time length, may start at the onset of the given motor event, may start prior to the onset of the given motor event (e.g., 1 second prior to the onset of the motor event, may end a given period of time after the onset of the motor event (e.g., 1 second after the onset of the motor event). In some embodiments, the motor events may be identified in the LFP signals prior to bilaterally re-referencing the LFP signals.

At block 315, a time-frequency domain transform may be applied to the bilaterally re-referenced LFP signals. For example, a continuous wavelet transform (CWT) may be applied to the bilaterally re-referenced LFP signals. Any other algorithm, mathematical function, and/or process may be used to create a time-frequency domain representation of the bilaterally re-referenced LFP signals. For example, a complex Morlet (C-Morlet) mother wavelet transform can be used:

$$X_w(a, b) = \int_{-\infty}^{+\infty} \frac{x(t)}{\sqrt{a}} \psi\left(\frac{t-b}{a}\right) dt,$$

$$\psi(t) = \frac{e^{-t^2/f_b}}{\sqrt{\pi f_b}} e^{j2\pi f_c t},$$

where, $X_\omega(a,b)$ is the CWT of the function x(t) with two variables a (scaling parameter) and b (shift parameter). Ψ(t) is the C-Morlet mother wavelet. $f_c$ and $f_b$ are respectively the wavelet center frequency and bandwidth parameter. In some embodiments, the β frequency components may be of interest and/or $f_c$ can be set in the appropriate frequency range (e.g., 13-35 Hz).

In some embodiments, the time-frequency domain transform may return a two dimensional spectrograph for each channel. Each spectrograph may be a matrix of time-frequency values for a given channel. Two sets of spectrograph data may be returned: one set for the right hemisphere and another set for the left hemisphere. In some embodiments, the spectrograph data may include a spectrograph for each channel.

Figure 4:
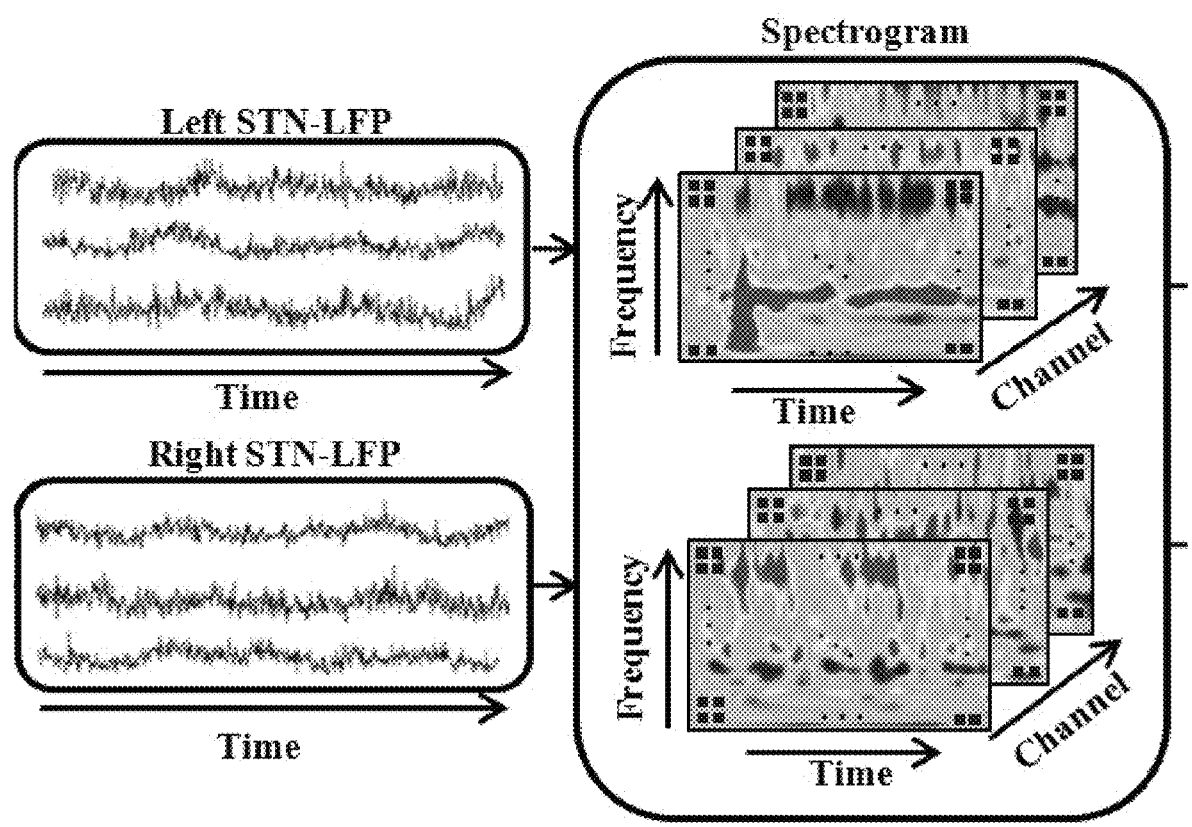
FIG. 4 is a graphic showing three LFP signals from the left hemisphere converted into three spectrographs; one for each channel.

FIG. 4 is a graphic showing three LFP signals from the left hemisphere converted into three spectrographs; one for each channel. The graphic in FIG. 4 also shows three LFP signals from the right hemisphere converted into three spectrographs; one for each channel.

At block 320, wavelet coefficients in a given frequency range can be found for the motor event windows identified in block 310 by solving the equations noted above for the CWT and/or the C-Morlet mother wavelet.

At block 325, in some embodiments, the spectrographs can be converted into vectors. For example, each matrix of spectrograph values may be converted into a vector. This may be accomplished, for example, by arranging the columns or the rows of the matrix in a vector.

At block 330, in some embodiments, the spectrograph vectors may optionally be filtered. For instance, the spectrograph vectors may be low-pass filtered using any type of filtering algorithm such as, for example, the Butterworth filter of any order. These spectrograph vectors may be used as feature vectors in a machine learning algorithm.

At block 335, in some embodiments, the spectrograph vectors may optionally be down-sampled. This down-sampling, for example, may provide a smaller data set to improve computational costs and/or efficiencies. In some embodiments, down sampling may not be needed.

At block 340 a machine learning classifier can be applied to the spectrograph vectors of both left hemisphere LFP data and right hemisphere LFP data. Any type of machine learning classifier can be use such as, for example, a multiple kernel learning classifier, may be used to classify the LFP signals data with the motor event identified in block 310. Any type of machine learning or supervised learning algorithm can be used. For example, the machine learning classifier may include supervised learning, semisupervised learning, or unsupervised learning approaches. In some embodiments, an $l_p$-norm classifier may be used.

Figure 5:
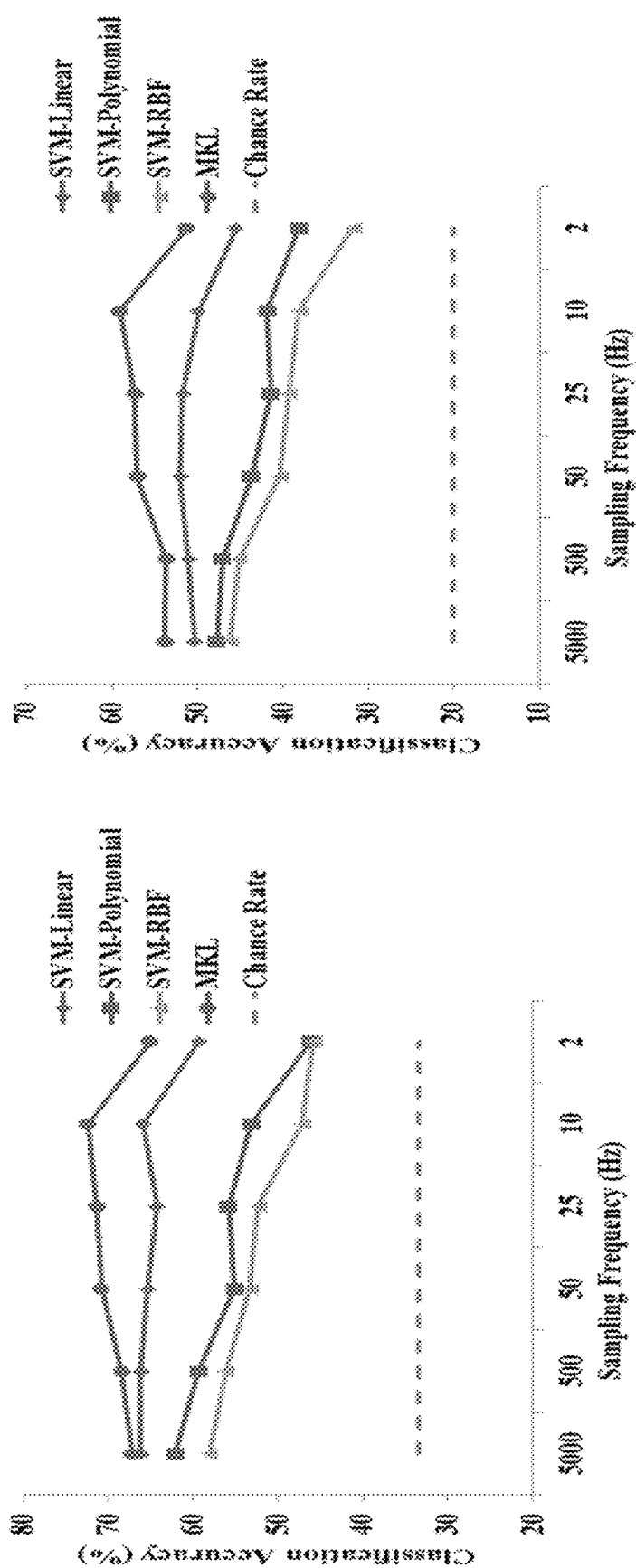
FIG. 5 shows two graphs showing the classification accuracy (%) of different classification methods vs. sampling frequency.

FIG. 5 shows two graphs showing the classification accuracy (%) of different classification methods vs. sampling frequency. Left and right graphs respectively show the results for 3-task (Speech, Button press, Random segment) and 5-task (Speech, Button press, Arm movement, Mouth movement, and Random segment) classification respectively. The random segments were used to train the classifier to recognize other tasks rather than the known tasks. The "Chance Rate" is included in the graphs to show the qualification of each classifier. If the accuracy is below the "Chance Rate", it means that the classifier is not a suitable choice; it is nothing but a random operator.

FIG. 5 shows that the presented $l_p$-norm MKL classifier outperforms the other compared classifiers. In the example experiments, the results of the MKL classifier are robust even when the sampling frequency of the feature vectors is drastically low. To measure the robustness of different methods against the size of the feature vectors, all the experiments are redone for different down-sampling rates.

Some embodiments include processing of a plurality of LFP signals. In some embodiments, the various channels may be blended prior to classification. In some embodiments, one or more channels may be selected based on correlation and/or synchronization of the signals. For example, a channel from each hemisphere may be selected based on the highest synchronization and/or correlation of the signals. In some embodiments, an FFT-based synchronization approach may be used to select (e.g., automatically select) an FFT-based synchronization approach to select a relevant pair of LFP signals and use the pair together with a classifier (e.g., an MKL-based SVM), for example, for behavior recognition purposes.

Figure 6:
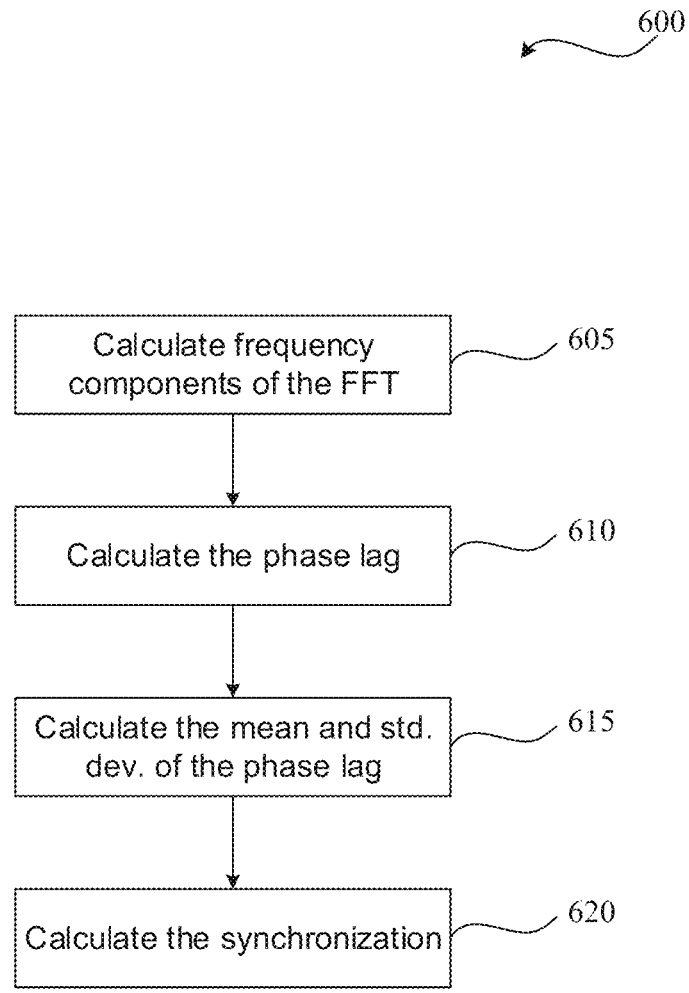
FIG. 6 illustrates a flowchart of an example process 300 that may be performed according to some embodiments

In some embodiments, an FFT-based approach may be used to find a synchronous pair of LFP signals in each, which may provide a reliable dataset for training an employed classifier. An LFG signal may have many phase values associated with each Fourier components. The FFT-based synchronization considers the phase values of each frequency component separately, which may, for example, lead to a more minute measure of phase synchronization based on a finer resolution compared to the statistical correlation-based measures. In some embodiments, the FFT-based approach may be independent of the amplitude of signal FIG. 6 is a flowchart of an example process 600 of an FFT-based approach for determining whether two LFP signals are synchronized according to some embodiments. The process 600 is merely an example and variations may be present. As another example, additional blocks or steps may be included. As another example, one or more blocks or steps may not be included. The process 600 may, for example, be executed and/or controlled at least in part with a computational system 1000 shown in FIG. 10.

Process 600 may be used to determine whether two LFP signals are synchronized. The process 600 may be repeated any number of times to compare the synchronization between any two LFP signals. The process 600, for example, may be implemented in conjunction with process 100 such as, for example, after block 120. In some embodiments, the two signals may include a right hemisphere signal and a left hemisphere signal.

At block 605 the frequency components of the LFP signals may be calculated. For example, the FFT coefficients $a_{in}$, $b_{in}$, $a_{jn}$, and $b_{jn}$ may be calculated for the $n^{th}$ frequency component for the left hemisphere, i, and the right hemisphere, j using any FFT protocol or algorithm. In some embodiments, additional FFT coefficients may be calculated. The corresponding phase components $\theta_{in}$ and $\theta_{jn}$ may also be calculated from:

$$\theta_{in} = \tan^{-1}\left(\frac{a_{in}}{b_{in}}\right),\ \theta_{jn} = \tan^{-1}\left(\frac{a_{jn}}{b_{jn}}\right).$$

At block 610 the phase lag of the LFP signals may also be calculated. For instance, two LFP signals may be considered synchronous when the phase components, $\theta_{in}$ and $\theta_{jn}$, are almost equal. For the nth frequency component the phase lag, PL, value may be calculated from:

$$PL(n) = |\theta_{in} - \theta_{jn}| \approx 0 \Rightarrow PL(n) = \left|\frac{a_{in}b_{jn} - b_{in}a_{jn}}{a_{in}a_{jn} + b_{in}b_{jn}}\right| \approx 0.$$

In some embodiments, the phase lag values for all (or a plurality of) harmonics may be taken into account.

At block 615, the mean and/or standard deviation of the calculated phase lag values may be calculated. The two LFP signals may be considered to be synchronous, for example, when the mean and/or standard deviation values of the phase lag are low At block 620 the synchronization of the two LFP signals may be calculated such as, for example, from:

$$\text{sync}(x_i(t), x_j(t)) = \frac{1}{1 + \text{mean}(E(n)) + std(E(n))};$$

and, in some embodiments:

$$E(n) = |PL(n) - PL(n+1)| = \frac{a_{in}b_{jn} - b_{in}a_{jn}}{a_{in}a_{jn} + b_{in}b_{jn}} - \frac{a_{in+1}b_{jn+1} - b_{in+1}a_{jn+1}}{a_{in+1}a_{jn+1} + b_{in+1}b_{jn+1}},$$

where, mean(•) and std(•) are respectively the average and standard deviation of the quantity E(n) calculated across all the frequency components. These equations may guarantee that the synchronization values are normalized in the range of [0, 1], so the more phase synchronous two signals are the closer to 1 is the value of sync(•). The synchronization may be calculated for all possible LFP pairs.

In some embodiments, one of the main advantages of the FFT-based synchronization is the low computational complexity, which may be equal to that of the FFT algorithm. As a result, this approach might lead to near optimal LFP pairs for each subject without imposing any further computational burden.

In some embodiments, process 600 may be used to select LFP pairs for classification such as, for example, the MKL-based SVM classifier described in process 300.

Figure 7:
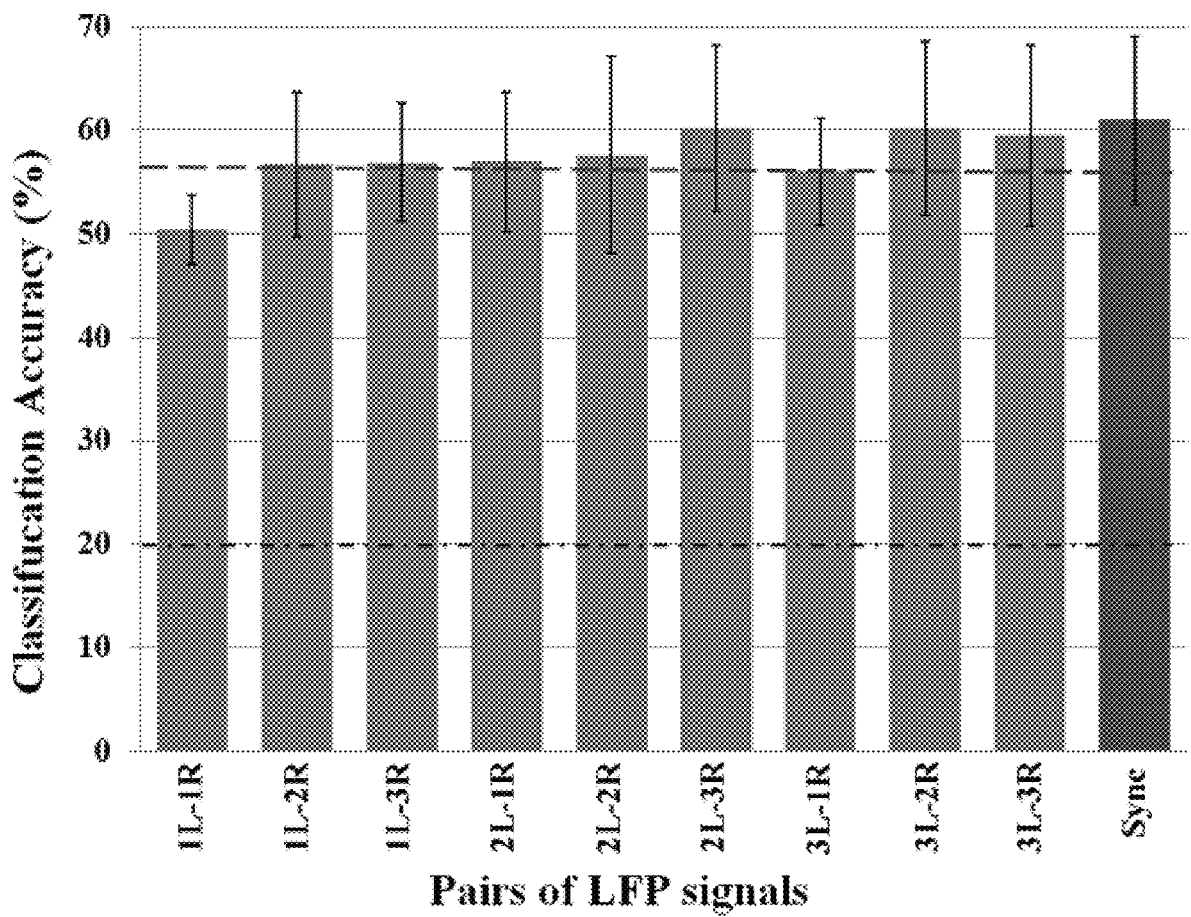
FIG. 7 shows is a graph showing the average classification accuracy of the MKL approach for all LFP pairs.

FIG. 7 shows is a graph showing the average classification accuracy of the MKL approach for all LFP pairs. The red bar on the far right shows the result using the FFT synchronization. The red dash-line shows the average of all 9 blue bars, and the black dash-dot line represents the chance rate.

In particular, the average classification accuracy given by the LFP pair 3L-2R (60.22%) is comparable to that of the FFT synchronization approach (61%). However, while c) the synchronization method can automatically select the optimal LFP pair for each subject without imposing a considerable computational cost (i.e., the computational time is no longer than the FFT algorithm), it may be useful to repeat the time-consuming training and validation phases for all possible LFP pairs to get the optimal pair in each case.

FIG. 8A is a drawing showing example placements of an electrode inserted within a human brain. FIG. 8B is a drawing showing an electrode inserted into the globus pallidus of the human brain. FIG. 8C is a drawing showing an electrode inserted into the subthalmic nucleus of the human brain. In some embodiments, the electrode may be inserted into any portion of the human brain. The electrodes may be coupled with a pulse generator that may, for example, be placed subcutaneously within the human. The electrodes, for example, may be connected with the pulse generator via an electrode lead. Various other electrode configurations and/or electrode placements may be used without limitation.

Figure 9A:
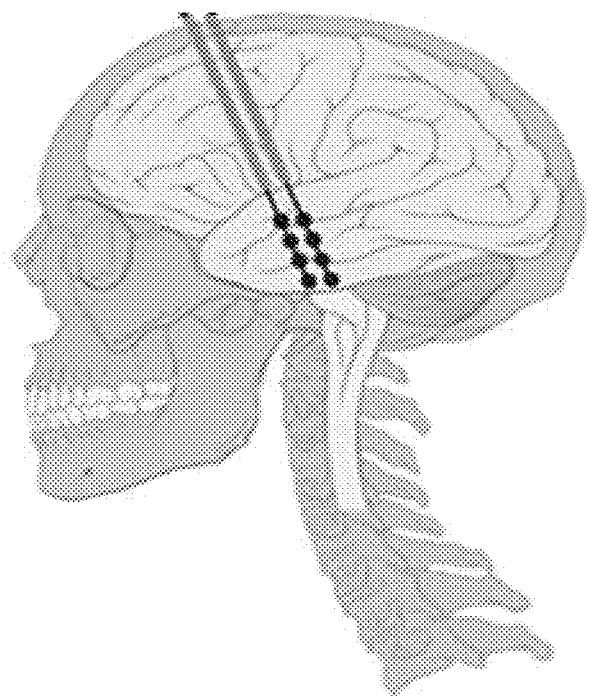
FIG. 9A is a drawing showing two probes inserted into a human brain.
Figure 9B:
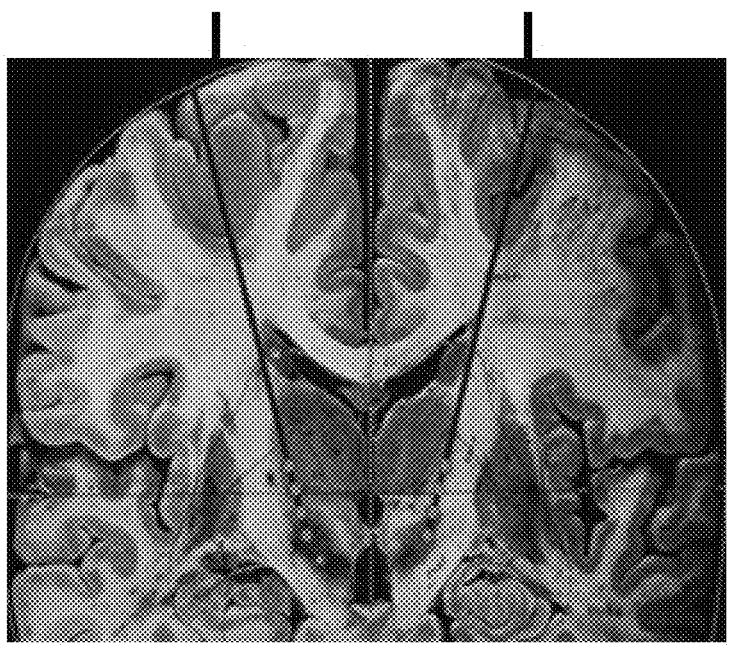
FIG. 9B is an MRI scan showing two probes inserted into a human brain.

FIG. 9A is a drawing showing two probes inserted into a human brain. FIG. 9B is an MRI scan showing two probes inserted into a human brain.

Figure 10:
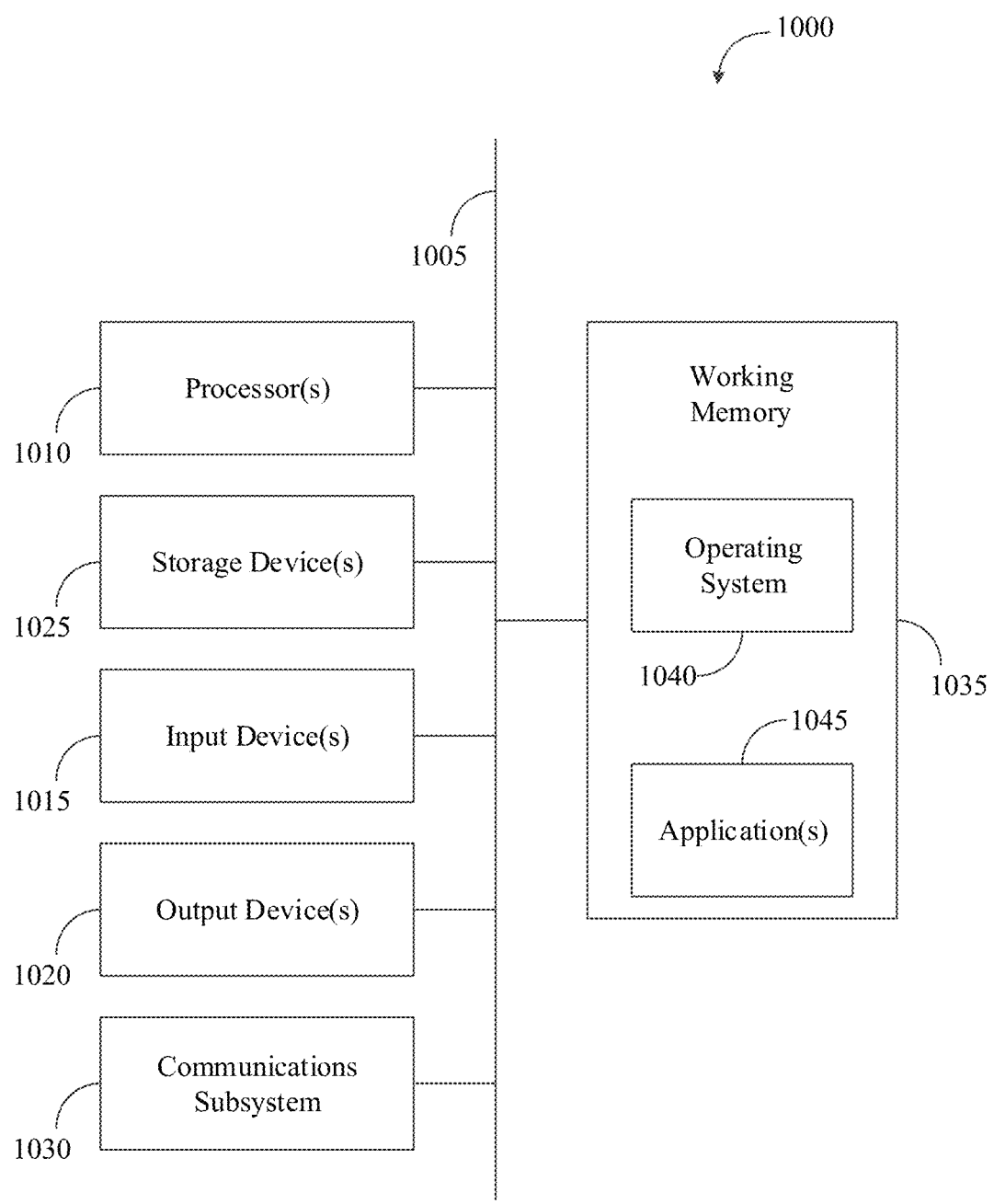
FIG. 10 shows an illustrative computational system for performing functionality to facilitate implementation of embodiments described herein.

The various flowcharts, processes, computers, servers, etc. described in this document may be executed, for example, using the computational system 1000 (or processing unit) illustrated in FIG. 10. For example, the computational system 1000 can be used alone or in conjunction with other components. As another example, the computational system 1000 can be used to perform any calculation, solve any equation, perform any identification, and/or make any determination described here.

The computational system 1000 may include any or all of the hardware elements shown in the figure and described herein. The computational system 1000 may include hardware elements that can be electrically coupled via a bus 1005 (or may otherwise be in communication, as appropriate). The hardware elements can include one or more processors 1010, including, without limitation, one or more general-purpose processors and/or one or more special-purpose processors (such as digital signal processing chips, graphics acceleration chips, and/or the like); one or more input devices 1015, which can include, without limitation, a mouse, a keyboard, and/or the like; and one or more output devices 1020, which can include, without limitation, a display device, a printer, and/or the like.

The computational system 1000 may further include (and/or be in communication with) one or more storage devices 1025, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational system 1000 might also include a communications subsystem 1030, which can include, without limitation, a modem, a network card (wireless or wired), an infrared communication device, a wireless communication device, and/or chipset (such as a Bluetooth® device, a 802.6 device, a Wi-Fi device, a WiMAX device, cellular communication facilities, etc.), and/or the like. The communications subsystem 1030 may permit data to be exchanged with a network (such as the network described below, to name one example) and/or any other devices described herein. In many embodiments, the computational system 1000 will further include a working memory 1035, which can include a RAM or ROM device, as described above.

The computational system 1000 also can include software elements, shown as being currently located within the working memory 1035, including an operating system 1040 and/or other code, such as one or more application programs 1045, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1025 described above.

In some cases, the storage medium might be incorporated within the computational system 1000 or in communication with the computational system 1000. In other embodiments, the storage medium might be separate from the computational system 1000 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 1000 and/or might take the form of source and/or installable code, which, upon compilation and/or installation on the computational system 1000 (e.g., using any of a variety of generally available compilers, installation programs, compression/decompression utilities, etc.), then takes the form of executable code.

The term "substantially" means within 5% or 10% of the value referred to or within manufacturing tolerances.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

All examples and conditional language recited in the present disclosure are intended for pedagogical objects to aid the reader in understanding the invention and concepts contributed by the inventor to furthering the art, and are to be construed as being without limitation to such specifically recited examples and conditions. Although embodiments of the present disclosure have been described in detail, various changes, substitutions, and alterations could be made hereto without departing from the spirit and scope of the present disclosure.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

That which is claimed:

1. A system comprising:
    a first plurality of probes configured to detect electrophysiological signals when inserted into a human brain;
    a second plurality of probes configured to detect electrophysiological signals when inserted into a human brain;
    an electronic data storage; and
    a processor electronically coupled with the first plurality of probes, the second plurality of probes; and the electronic data storage, wherein the processor performs at least the following:
        receiving a first plurality of electrophysiological signals from the first plurality of probes;
        recording the first plurality of electrophysiological signals in the electronic data storage;
        receiving a second plurality of electrophysiological signals from the second plurality of probes;
        recording the second plurality of electrophysiological signals in the electronic data storage;
        pre-processing the first plurality of electrophysiological signals and the second plurality of electrophysiological signals;
        bipolar re-referencing the first plurality of electrophysiological signals and the second plurality of electrophysiological signals;
        determining an optimal pair of electrophysiological signals from the bipolar re-referenced first plurality of electrophysiological signals and the bipolar re-referenced second plurality of electrophysiological signals;
        matching the optimal pair of electrophysiological signals with a brain excitation template stored within the electronic data storage; and
        detecting motor events based on the matching.

2. The system according to claim 1, further comprising a multiple kernel learning classifier configured to classify the motor events.

3. The system according to claim 1, wherein the processor is configured to perform a non-linear regression on the bipolar re-referenced first plurality of electrophysiological signals and second plurality of electrophysiological signals prior to the determining of the optimal pair of electrophysiological signals.

4. The system according to claim 1, wherein the optimal pair of electrophysiological signals are determined by performing a nonlinear regression on the bipolar re-referenced first plurality of electrophysiological signals and the bipolar re-referenced second plurality of electrophysiological signals.

5. The system according to claim 4, wherein the nonlinear regression may produce a measure of inter-correlation between each of the bipolar re-referenced first plurality of electrophysiological signals and each of the bipolar re-referenced second plurality of electrophysiological signals.

6. The system according to claim 1, wherein the optimal pair of electrophysiological signals are determined from a time-frequency transform applied to the electrophysiological signals.

7. The system according to claim 1, wherein the matching the optimal pair of electrophysiological signals with a template includes applying a principal component analysis on the template and the bipolar re-referenced first plurality of electrophysiological signals and the bipolar re-referenced second plurality of electrophysiological signals to obtain normalized correlation coefficients.

8. The system according to claim 1, wherein bipolar re-referencing the first plurality of electrophysiological signals and the second plurality of electrophysiological signals comprises:
    subtracting each of the first plurality of electrophysiological signals from another of the first plurality of electrophysiological signals; and
    subtracting each of the second plurality of electrophysiological signals from another of the second plurality of electrophysiological signals.

9. The system according to claim 1, wherein the processor further performs at least the following comprising:
    determining an optimal first electrophysiological signal and an optimal second electrophysiological signal from a nonlinear regression.

10. The system according to claim 1, wherein the electrophysiological signals comprise local field potential (LFP) signals.

11. A method comprising:
    recording a first plurality of electrophysiological signals from a first plurality of probes inserted into the left hemisphere of a brain;
    recording a second plurality of electrophysiological signals from a second plurality of probes inserted into the right hemisphere of the brain; with a processor: and
    pre-processing the first plurality of electrophysiological signals and the second plurality of electrophysiological signals;
    bipolar re-referencing the first plurality of electrophysiological signals and the second plurality of electrophysiological signals;
    determining an optimal pair of electrophysiological signals from the bipolar re-referenced first plurality of electrophysiological signals and the bipolar re-referenced second plurality of electrophysiological signals;
    matching the optimal pair of electrophysiological signals with a template; and
    detecting motor events from the matching.

12. The method according to claim 11, wherein the optimal pair of electrophysiological signals are determined by performing a nonlinear regression on the bipolar re-referenced first plurality of electrophysiological signals and the bipolar re-referenced second plurality of electrophysiological signals.

13. The method according to claim 12, wherein the nonlinear regression may produce a measure of inter-correlation between each of the bipolar re-referenced first plurality of electrophysiological signals and each of the bipolar re-referenced second plurality of electrophysiological signals.

14. The method according to claim 11, wherein the optimal pair of electrophysiological signals are determined from a time-frequency transform applied to the electrophysiological signals.

15. The method according to claim 11, wherein the matching the optimal pair of electrophysiological signals with a template includes applying a principal component analysis on the template and the bipolar re-referenced first plurality of electrophysiological signals and the bipolar re-referenced second plurality of electrophysiological signals to obtain normalized correlation coefficients.

16. The method according to claim 11, wherein bipolar re-referencing the first plurality of electrophysiological signals and the second plurality of electrophysiological signals comprises:
    subtracting each of the first plurality of electrophysiological signals from another of the first plurality of electrophysiological signals; and
    subtracting each of the second plurality of electrophysiological signals from another of the second plurality of electrophysiological signals.

17. The method according to claim 11, further comprising:
    determining an optimal first electrophysiological signal and an optimal second electrophysiological signal from the linear regression.

18. One or more non-transitory computer-readable media storing one or more programs that are configured, when executed, to cause one or more processors to execute the method as recited in claim 11.

* * * * *